United States Patent
DeSantis, Jr.

(10) Patent No.: US 6,441,047 B2
(45) Date of Patent: *Aug. 27, 2002

(54) COMBINATION THERAPY FOR TREATING GLAUCOMA

(75) Inventor: Louis DeSantis, Jr., Fort Worth, TX (US)

(73) Assignee: Alcon Manufacturing Ltd.., Ft. Worth (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/267,966

(22) Filed: Mar. 12, 1999

Related U.S. Application Data

(63) Continuation-in-part of application No. 08/919,882, filed on Aug. 28, 1997, now Pat. No. 5,883,108, which is a continuation of application No. 08/560,055, filed on Nov. 17, 1995, now abandoned.

(51) Int. Cl.$^7$ .............................................. A61K 31/135

(52) U.S. Cl. ........................................ 514/649; 514/913

(58) Field of Search ................................. 514/649, 913

(56) References Cited

U.S. PATENT DOCUMENTS

| | | | |
|---|---|---|---|
| 4,540,408 A | 9/1985 | Lloyd | 604/294 |
| 4,599,353 A | 7/1986 | Bito | 514/530 |
| 4,690,931 A | 9/1987 | Wick et al. | 514/317 |
| 4,730,013 A | 3/1988 | Bondi et al. | 524/42 |
| 4,797,413 A | 1/1989 | Baldwin et al. | 514/432 |
| 4,861,760 A | 8/1989 | Mazuel et al. | 514/54 |
| 4,911,920 A | 3/1990 | Jani et al. | 424/78 |
| 5,093,329 A | 3/1992 | Woodward | 514/469 |
| 5,153,192 A | 10/1992 | Dean et al. | 514/226.5 |
| 5,212,162 A | 5/1993 | Missel et al. | 514/54 |
| 5,238,961 A | 8/1993 | Woodward et al. | 514/573 |
| 5,240,923 A | 8/1993 | Dean et al. | 514/226.5 |
| 5,262,437 A | 11/1993 | Chan | 514/530 |
| 5,312,842 A | 5/1994 | Chan | 514/708 |
| 5,321,128 A | 6/1994 | Stjernschantz et al. | 514/530 |
| 5,328,933 A | 7/1994 | Chan | 514/727 |
| 5,352,708 A | 10/1994 | Woodward et al. | 514/729 |
| 5,378,703 A | 1/1995 | Dean et al. | 514/222.8 |
| 5,403,841 A | 4/1995 | Lang et al. | 514/226.8 |
| 5,545,665 A | 8/1996 | Burk | 514/530 |
| 5,552,434 A | 9/1996 | Garst et al. | 514/548 |
| 5,688,819 A | 11/1997 | Woodward et al. | 514/357 |
| 5,922,773 A | * 7/1999 | Lipton et al. | |

FOREIGN PATENT DOCUMENTS

| | | | |
|---|---|---|---|
| EP | 215 860 B1 | 3/1986 | A61K/31/557 |
| EP | 0 299 914 B1 | 7/1993 | A61K/31/557 |
| WO | WO 94/13275 | 6/1994 | A61K/31/135 |
| WO | WO 97/30710 | 8/1997 | A61K/31/557 |

OTHER PUBLICATIONS

"Mechanisms of excitotoxicity in neurologic diseases", M. Flint Beal, *The FASEB Journal*, vol. 6, pp. 3338–3344, Dec., 1992.

"Excitotoxic Cell Death", Dennis W. Choi, *Journal of Neurobiology*, vol. 23, No. 9, pp. 1261–1276, (1992).

"Morphology of Quisqualate–Induced Neurotoxicity in the Chicken Retina", Sattayasai et al, *Investigative Ophthalmology & Visual Science*, vol. 28, pp. 106–117, Jan., 1987.

"A quantitative analysis of the effects of excitatory neurotoxins on retinal ganglion cells in the chick", Tung et al., *Visual Neuroscience*, vol. 4, pp. 217–223, (1990).

"Histologic changes in the inner retina of albino rats following intravitreal injection of monosodium L–glutamate", Sisk et al., *Graefe's Arch. Clin. Exp. Ophtahlmol.*, vol. 223, pp. 250–258, (1985).

"N–methyl–D–aspartate–induced neurotoxicity in the adult rat retina", Siliprandi et al., *Visual Neuroscience*, vol. 8, pp. 567–573, (1992).

"Effects of monosodium glutamate on chick embryo retina in culture", Reif–Lehrer et al., *Investigative Ophthalmology Visual Science*, vol. 14 No. 2, pp. 114–124, Feb. (1975).

"Effects of Monosodium Glutamate on the Isolated Retina of the Chick Embryo as a Function of Age: A Morphological Study", Blanks et al., *Exp. Eye Res.*, vol. 32, pp. 105–124, (1981).

"The role of specific ions in glutamate neurotoxicity", Olney et al., *Neuroscience Letters*, vol. 65, pp. 65–71, (1986).

"The anti–excitotoxic effects of certain anesthetics, analgesics and sedative–hypnotics", Olney et al., *Neuroscience Letters*, vol. 68, pp. 29–34 (1986).

"CNQX potently and selectively blocks kainate excitotoxicity in the chick embryo retina", Price et al., *Soc. Neuroscience Abstract*, vol. 14, p. 418 (1988).

Involvement of excitatory neurotransmitters in the damage produced in chick embryo retinas by anoxia and extracellular high potassium, David et al., *Exp. Eye Res.*, vol. 46, pp. 657–662 (1988).

"Large retinal ganglion cells are more susceptible to excitotoxic and hypoxic injury than small cells", Caprioli et al., *Inves Ophthalmol. Vis. Sci.*, vol. 34, p. 1429 (1993).

"Electrophysiology of Cultured Retinal Ganglion Cells to Investigate Basic Mechanisms of Damage", Cummins et al. *Glaucoma Update IV*, pp. 59–65 (1991).

"Cell types using glutamate as a neurotransmitter in the vertebrate retina", S. Massey, *Progress in Retinal Research*, N.N. Osborne and G. J. Chader (Eds.), Pergammon Press: Oxford, Ch. 11, pp. 399–425, (1990).

"Excitatory Amino Acid Receptors In the Vertebrate Retina", Miller et al., *Retinal Transmitters and Modulators: Models for the Brain*, (W. W. Morgan, Ed.), CRC Press, Inc., Boca Raton, II, pp. 123–160 (1985).

(List continued on next page.)

Primary Examiner—Zohreh Fay
(74) Attorney, Agent, or Firm—Sally Yieager

(57) ABSTRACT

Methods for treating persons with glaucoma or ocular hypertension with glutamate antagonists and IOP-lowering compounds are disclosed.

8 Claims, No Drawings

OTHER PUBLICATIONS

"N–methyl–D–aspartate Antagonists Prevent Kainate Neurotoxicity in Rat Retinal Ganglion Cells in vitro", Sucher et al., *The Journal of Neuroscience*, vol. 11, No. 4, pp. 966–967, Apr., 1991.

"Action of the anti–ischemic agent ifenprodil on N–methyl–D–aspartate and kainate–mediated excitotoxicity", Zeevalk et al., *Brain Research*, vol. 522, pp. 135–139 (1990).

"Glutamate in CNS Disorders as a Target for Drug Development: An Update", Parsons et al., *Drug News Perspect*, vol. 11, No. 9, pp. 523–569 (Nov. 1998).

"A Novel Ocular Hypotensive Lipid™: Initial Safety and Efficacy of AGN 192024", VanDenburgh, et al., Abstract 1177–B58, *IOVS*, Mar. 15, 1998, vol. 39, No. 4, p. S258.

"Eliprodil Hydrochloride" Scatton, et al., *Drugs of the Future*, vol. 19(10):905–909, (1994).

* cited by examiner

COMBINATION THERAPY FOR TREATING GLAUCOMA

This case is a continuation in part of U.S. Ser. No. 08/919,882, filed Aug. 28, 1997 now U.S. Pat. No. 5,883,108, which is a continuation of U.S. Ser. No. 08/560,055, filed Nov. 17, 1995.

The present invention relates generally to the field of ophthalmology. In particular, the invention relates to the treatment of glaucoma using a combination of a glutamate antagonist to preserve visual field and an intraocular pressure lowering compound.

BACKGROUND OF THE INVENTION

Although the underlying causes of glaucoma are not well understood at this time, glaucoma is characterized by damage to the optic nerve, accompanied by a decrease in the normal visual field. One early warning sign of possible glaucomatous visual field loss is elevated intraocular pressure ("IOP"). In fact, glaucoma has historically been treated by medically and /or surgically lowering elevated IOP, for example, by the administration of IOP-lowering agents such as miotics, α and α/β adrenergic agonists, beta-blockers, and carbonic anhydrase inhibitors. However, factors other than IOP may play a role in the occurrence of visual field loss. Degeneration of retinal ganglion cells may be related to ischemia or mechanical distortion of the nerve fibers as they exit through the optic nerve head or from pathological perturbations of the retina.

There has been a growing interest in retinal dysfunction as a contributor to the glaucomatous process. Retinal dysfunction, and hence pathology, may be related to ischemia or excitotoxicity. Excitotoxicity is neuronal injury due to excessive excitatory amino acid ("EAA") stimulation. In the inner retina, glutamate is the major EAA that permits the bipolar and amacrine cells to communicate with the ganglion cell. In the central nervous system, excitotoxicity results from hypoxia, ischemia, hypoglycemia or trauma. (See, for example, Beal, M. F., "Mechanisms of excitotoxicity in neurologic diseases," *FASEB J.*, 6:3338–3344 (1992); and Choi, D. W., "Excitotoxic cell death," *J. Neurobiol.*, 23:1261–1276 (1992).) Toxicity to the inner retina has been observed following intravitreal injection of EAAs following application of EAAs to the isolated animal retina or from exogenously applied glutamate to retinal ganglion cells in culture. See generally, Sattayasai, et al., "Morphology of quisqualate-induced neurotoxicity in the chicken retina," *Invest. Ophthalmol. Vis. Sci.*, 28:106–117 (1987); Tung et al., "A quantitative analysis of the effects of excitatory neurotoxins on retinal ganglion cells in the chick," *Visual Neurosci.*, 4:217–223 (1990); Sisk et al., "Histological changes in the inner retina of albino rats following intravitreal injection of monosodium L-glutamate," *Graefe's Arch. Clin. Exp. Ophthalmol.*, 223:250–258 (1985); Siliprandi et al., "N-methyl-D-aspartate-induced neurotoxicity in the adult rat retina," *Visual Neurosci.*, 8:567–573 (1992); Reif-Lehrer et al., "Effects of monosodium glutamate on chick embryo retina in culture," *Invest. Ophthalmol. Vis. Sci.*, 14(2):114–124 (1975); Blanks, J. C., "Effects of monosodium glutamate on the isolated retina of the chick embryo as a function of age: A morphological study," *Exp. Eye Res.*, 32:105–124 (1981); Olney et al., "The role of specific ions in glutamate neurotoxicity," *Neurosci. Lett.*, 65:65–71 (1986); Olney et al., "The anti-excitotoxic effects of certain anesthetics, analgesics and sedative-hypnotics," *Neurosci. Lett* 68:29–34 (1986); Price et al., "CNQX potently and selectively blocks kainate excitotoxicity in the chick embryo retina," *Soc. Neurosci. Abst.*, 14:418 (1988); David et al., "Involvement of excitatory neurotransmitters in the damage produced in chick embryo retinas by anoxia and extracellular high potassium," *Exp. Eye Res.*, 46:657–662 (1988); Caprioli et al., "Large retinal ganglion cells are more susceptible to excitotoxic and hypoxic injury than small cells *Invest. Ophthalmol. Vis. Sci.*, 34(Suppl):1429 (1993); Cummins et al., "Electrophysiology of cultured retinal ganglion cells to investigate basic mechanics of damage," *Glaucoma Update IV*, 59–65 (1991); and Sucher et al., "N-methyl-D-aspartate antagonists prevent kainate neurotoxicity in rat retinal ganglion cells in vitro," *J. Neurosci.*, 11(4):966–971 (1991).

EAA receptors have been characterized as metabotropic or ionotropic. Activation of a metabotropic receptor affects cellular processes via G-proteins; whereas ionotropic receptors affect the translocation of mono- and divalent cations across the cell membrane. There are at least three ionotropic receptors that have been named for the agonist that preferentially stimulates the receptor. These receptors have been classified as: N-methyl-D-aspartate (NMDA); kainate; and AMPA (2-amino-3-(3-hydroxy-5-methylisoxazol-4-yl) propanoic acid). These EAA receptors are differentially distributed to specific cells in the retina. (See, for example, Massey, S., "Cell types using glutamate as a neurotransmitter in the vertebrate retina," N. N. Osborne and G. J. Chader (Eds.) *Progress in Retinal Research*, Ch. 9, Pergammon Press: Oxford, 399–425 (1990); and Miller et al., "Excitatory amino acid receptors in the vertebrate retina," in *Retinal Transmitters and Modulators: Models for the Brain*, (W. W. Morgan, Ed.) CRC Press, Inc., Boca Raton, II:123–160 (1985).) The localization of such receptors would account for the pathologies associated with glaucoma or inner retinal ischemia. For example, death of the retinal ganglion cell has to a large part been attributed to the NMDA receptor. (See, for example, Sucher et al., "N-methyl-D-aspartate antagonists prevent kainate neurotoxicity in retinal ganglion cells in vitro," *J. Neurosci.*, 11(4):966–971 (1991).). Thus, antagonists of the NMDA receptor are neuroprotective; however, not all antagonists of the diversely distributed EAA receptors are neuroprotective to the inner retina through antagonism of the NMDA receptor, Zeevalk et al., "Action of the anti-ischemic agent ifenprodil on N-methyl-D-aspartate and kainate-mediated excitotoxicity," *Brain Res.*, 522:135–139 (1990)), and many of these EAA antagonists have significant CNS side-effects and are therefore not suitable for treating these degenerative diseases of the eye.

SUMMARY OF THE INVENTION

The present invention is directed to the use of a glutamate antagonist and an IOP controlling agent, dosed separately or in combination for the treatment of persons suffering from glaucoma or ocular hypertension.

DETAILED DESCRIPTION OF THE INVENTION

The present invention involves the use of two types of agents to treat glaucoma and ocular hypertension. One agent is an IOP-lowering agent directed at preventing the damage to retinal ganglion cells brought on by mechanical, circulatory, and other poorly understood factors related to elevated IOP. The second agent is a glutamate antagonist used to prevent further damage to ganglion cells and optic nerve fibers from excitotoxicity.

As used herein the term glutamate antagonist means an antagonist of the NMDA receptor channel complex. NMDA receptor antagonists include channel blockers (agents that operate uncompetitively to block the NMDA receptor channel); receptor antagonists (agents that compete with NMDA or glutamate at the NMDA binding site); and agents acting at the glycine coagonist site or any of several modulation sites (e.g., zinc, magnesium, redox, or polyamine sites).

Glutamate antagonists which have been found to be particularly effective have the following structure:

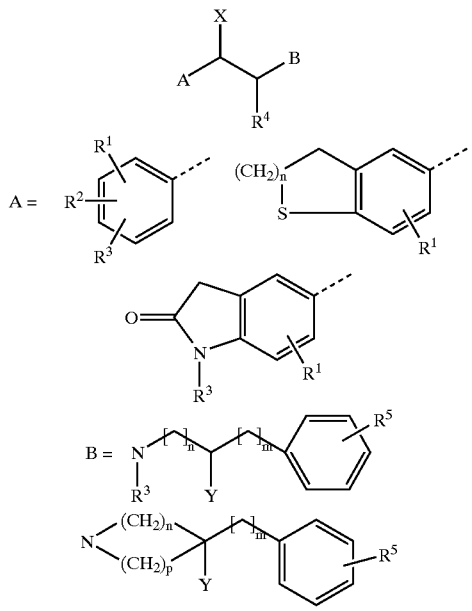

Y,X=OH,H
m=0–3
n,p=1,2
$R^1$=H, halogen, trifluoromethyl, C1–4 alkyl, OH, C1–4 alkoxy, benzyloxy, C1–16 alkanoyloxy, benzoyloxy or when $R^2$=OH or methoxy in the 4-position and $R^3$=H then $R^1$=hydroxymethyl, carbamoyl, or C1–4 alkoxycarbonyl;
$R^2$=H, halogen, C1–4 alkyl, OH, C1–4 alkoxyl;
$R^3$, $R^4$=H, C1–4 alkyl; and
$R^5$=H, halogen, trifluoromethyl, C1–4 alkyl, OH, C1–4 alkoxy, benzyloxy, C1–16 alkanoyloxy, benzoyloxy.

These compounds include all isomers and pharmaceutically acceptable salts.

Other preferred compounds include: amantadine, budipine, felbamate, cerestat (CNS-1102, aptiganel), dextromethorphan, dexanabinol, ADCI, araxins, CNS-5161, B111-277CL, WAY-126251 (see Drug News Perspect 11(9), November 1998), memantine, and other compounds disclosed in WO 94/13275 to the extent they are suitable for chronic administration.

In general, at least one of the compounds of this invention are administered orally with daily dosage of these compounds ranging between 0.01 and 500 milligrams. The preferred total daily dose ranges between 1 and 100 milligrams. Non-oral administration, such as, intravitreal, topical ocular, transdermal patch, parenteral, intraocular injection, or subconjunctival routes may require an adjustment of the total daily dose necessary to provide a therapeutically effect amount of the compound.

The compounds can be incorporated into various types of ophthalmic formulations for topical delivery to the eye. They may be combined with ophthalmologically acceptable preservatives, surfactants, viscosity enhancers, penetration enhancers, buffers, sodium chloride, and water to form aqueous, sterile ophthalmic suspensions or solutions. Ophthalmic solution formulations may be prepared by dissolving the compound in a physiologically acceptable isotonic aqueous buffer. Further, the ophthalmic solution may include an ophthalmologically acceptable surfactant to assist in dissolving the compound. The ophthalmic solutions may contain a thickener, such as, hydroxymethylcellulose, hydroxyethylcellulose, hydroxypropylmethylcellulose, methylcellulose, polyvinyl-pyrrolidone, or the like, to improve the retention of the formulation in the conjunctival sac. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940, or the like, according to the published formulations for analogous ophthalmic preparations; preservatives and tonicity agents can be incorporated.

If dosed topically, the compounds are preferably formulated as topical ophthalmic suspensions or solutions, with a pH of about 4 to 8. The compounds will normally be contained in these formulations in an amount 0.001% to 5% by weight, but preferably in an amount of 0.01% to 2% by weight. Thus, for topical presentation, 1 to 2 drops of these formulations would be delivered to the surface of the eye 1 to 4 times per day according to the routine discretion of a skilled clinician.

The preferred compound, eliprodil, is orally bioavailable, demonstrates a low incidence of adverse effects upon administration, and effectively crosses the blood-brain barrier (Drugs of the Future, 1994, 19, 905–909) indicating that effective concentrations are expected in the target tissue, the retina. The compound is described in U.S. Pat. No. 4,690,931, the contents of which are incorporated herein by reference.

The IOP-lowering agents useful in the present invention include all presently known IOP-lowering pharmaceuticals, including, but not limited to, miotics (e.g., pilocarpine, carbachol, and acetylcholinesterase inhibitors); α and α/β adrenergic agonists (e.g., epinephrine, dipivalylepinephrine, para-amino clonidine and brimonidine); beta-blockers (e.g., betaxolol, S-betaxolol, levobunolol, carteolol, and timolol); prostaglandins and their analogues and derivatives, such as, compounds disclosed in U.S. Pat. Nos. 4,599,353; 5,093,329; and 5,321,128 and in European Patent Nos. 0215 860 B1 and 0 299 914 B1; and carbonic anhydrase inhibitors (e.g., acetazolamide, methazolamide, and ethoxzolamide, and compounds disclosed in U.S. Pat. Nos. 5,153,192; 5,240,923; 5,378,703; and 4,797,413) and ocular hypertensive lipids, such as those compounds (neutral replacement of the carboxylic acid group of prostaglandin F2α e.g. AGN 192024) described in IOVS, Mar. 15, 1998, Vol. 39, No. 4; WO 97/30710, U.S. Pat. Nos. 5,238,961; 5,262,437; 5,328,933; 5,352,708; 5,312,842; 5,552,434; 5,545,665; 5,688,819. The preferred IOP-lowering agents are: timolol, betaxolol, S-betaxolol levobunolol, carteolol, pilocarpine, carbachol, epinephrine, dipivalyl epinephrine-αmethyl dipivalylepinephrine, brinzolamide, dorzolamide, unoprostone, latanoprost, travoprost, apraclonidine, and brimonidine.

One or more IOP-lowering agents will be administered systemically, or if in a topical formulation, at a concentration of between 0.001 and 5.0 wt %, preferably, 0.01 to 2.5 wt %, but preferably 0.001–0.005 for prostaglandins.

The IOP-lowering compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference.

In addition to the above-described principal ingredients, the IOP-lowering compositions of the present invention may further comprise various formulatory ingredients, such as antimicrobial preservatives and tonicity agents. Examples of suitable antimicrobial preservatives include: benzalkonium chloride, thimerosal, chlorobutanol, methyl paraben, propyl paraben, phenylethyl alcohol, edetate disodium, sorbic acid, Polyquad® and other agents equally well-known to those skilled in the art. Such preservatives, if utilized, will typically be employed in an amount between about 0.001 and about 1.0 wt %. Examples of suitable agents which may be used to adjust the tonicity or osmolality of the formulations include: sodium chloride, potassium chloride, mannitol, dextrose, glycerin, and propylene glycol. Such agents, if utilized, will typically be employed in an amount between about 0.1 and about 10.0 wt %.

As will be appreciated by those skilled in the art, the compositions may be formulated in various dosage forms suitable for topical ophthalmic delivery, including solutions, suspensions, emulsions, gels, and erodible solid ocular inserts. The compositions are preferably aqueous suspensions or solutions.

The compositions of the present invention may also comprise non-aqueous formulations such as: substantially non-aqueous liquids substantially non-aqueous semi-solid compositions and solid compositions or devices.

The first class, substantially non-aqueous liquids, comprise an IOP-lowering agent and a second agent ("drug combination") dissolved or suspended in one or more of the following: vegetable and mineral oils, such as, liquid petrolatum, corn oil, castor oil, sesame oil, and peanut oil; triglycerides, such as the capric/caprylic triglycerides commonly used in foods and cosmetics; liquid lanolin and lanolin derivatives; and perfluorohydrocarbons.

The second class, semi-solid compositions, comprise an IOP-lowering agent dissolved or suspended in one or more of the following: various types of petrolatum, such as white, yellow, red and so on; lanolin and lanolin derivatives; gelled mineral oil having a hydrocarbon base, such as Plastibase(g; petrolatum and ethylene carbonate mixtures; petrolatum in combination with surfactants and polyglycol, such as polyoxyl 40 stearate and polyethylene glycol.

The third class, solid compositions or devices, include non-erodible devices which are inserted into the conjunctival sac of the eye and later removed, such as the Alza-type diffusion or osmotic pressure controlled polymer membranes; and bioerodible polymers which do not have to be removed from the conjunctival sac, such as essentially anhydrous but water soluble polymers and resins (e.g., celluloses, polycarboxylic acids, and so on). Especially preferred are the bioerodible inserts described and detailed in U.S. Pat. No. 4,540,408 (Lloyd) and U.S. Pat. No. 4,730,013 (Bondi et al.), wherein drug combinations of the present invention would be entrained in a non-aqueous matrix consisting essentially of polyvinyl alcohol. The entire contents of these two patents are incorporated herein by reference.

The present invention is also directed to methods of treating persons with glaucoma or ocular hypertension. At least one glutamate antagonist will be administered systemically and at least one IOP-lowering composition described above is applied topically to the affected eye(s) of the patient. The frequency and amount of dosage will be determined by the clinician based on various clinical factors. The methods will typically comprise topical application of one or two drops (or an equivalent amount of a solid or semi-solid dosage form) to the affected eye one to four times per day.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

I claim:

1. The method for treating a person suffering from glaucoma or ocular hypertension which comprises, administering at least one glutamate antagonist wherein the glutamate antagonist has the structure:

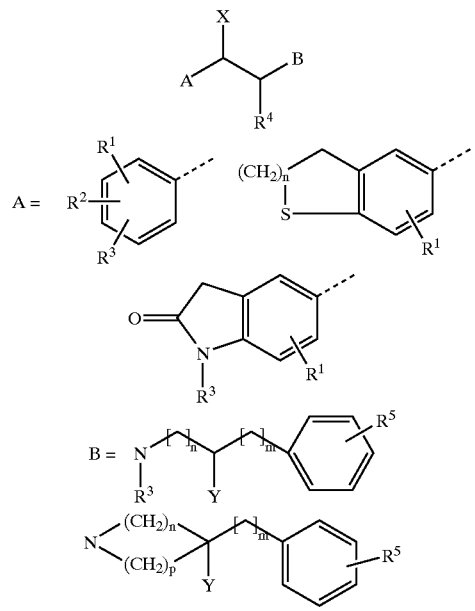

Y,X=OH, H m=0–3 n, p=1,2

$R^1$=H, halogen, trifluoromethyl, C1–4 alkyl, OH, C1–4 alkoxy, benzyloxy, C1–16 alkanoyloxy, benzoyloxy or when $R^2$=OH or methoxy in the 4-position and $R^3$=H then $R^1$=hydroxymethyl, carbamoyl, or C1–4 alkoxycarbonyl;

$R^2$=H, halogen, C1–4 alkyl, OH, C1–4 alkoxyl;

$R^3$, $R^4$=H, C1–4 alkyl; and $R^5$=H, halogen, trifluoromethyl, C1–4 alkyl, OH, C1–4 alkoxy, benzyloxy, C1–16 alkanoyloxy, benzoyloxy and all isomers and pharmaceutically acceptable salts and at least one intraocular pressure lowering agent.

2. The method of claim 1 wherein the IOP-lowering agent is selected from the group consisting of miotics, α and α/β adrenergic agonists, beta-blockers, prostaglandins, and carbonic anhydrase inhibitors.

3. The method of claim 2 wherein the IOP-lowering agent is betaxolol or S-betaxolol.

4. The method of claim 2 wherein the IOP-lowering agent is brimonidine.

5. The method of claim 2 wherein the IOP-lowering agent is latanoprost.

6. The method of claim 2 wherein the IOP-lowering agent is travoprost.

7. The method of claim 2 wherein the IOP-lowering agent is timolol.

8. A composition comprising a glutamate antagonist with the following structure:

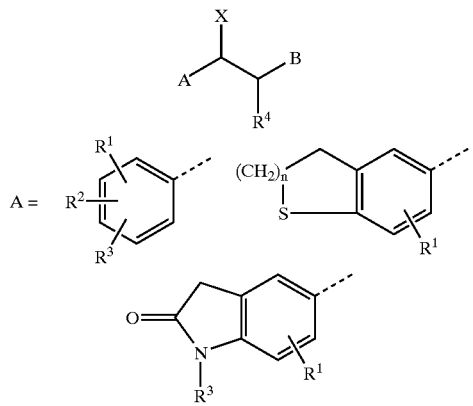

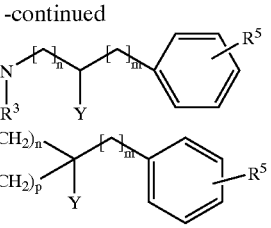

Y,X=OH, H m=0–3 n, p=1,2

$R^1$=H, halogen, trifluoromethyl, C1–4 alkyl, OH, C1–4 alkoxy, benzyloxy, C1–16 alkanoyloxy, benzoyloxy or when $R^2$=OH or methoxy in the 4-position and $R^3$=H then $R^1$=hydroxymethyl, carbamoyl, or C1–4 alkoxycarbonyl;

$R^2$=H, halogen, C1–4 alkyl, OH, C1–4 alkoxyl;

$R^3$, $R^4$=H, C1–4 alkyl; and $R^5$=H, halogen, trifluoromethyl, C1–4 alkyl, OH, C1–4 alkoxy, benzyloxy, C1–16 alkanoyloxy, benzoyloxy and all isomers and pharmaceutically acceptable salts and at least one intraocular pressure lowering agent.

* * * * *